United States Patent [19]

Wijesekera et al.

[11] Patent Number: 5,241,062

[45] Date of Patent: Aug. 31, 1993

[54] SYNTHETIC ROUTE TO MESO-TETRA HYDROCARBYL OR SUBSTITUTED HYDROCARBYL PORPHYRINS AND DERIVATIVES

[75] Inventors: Tilak P. Wijesekera, Glen Mills; Richard W. Wagner, Murrysville, both of Pa.

[73] Assignee: Sun Company, Inc. (R&M), Philadelphia, Pa.

[21] Appl. No.: 5,702

[22] Filed: Jan. 19, 1993

[51] Int. Cl.$^5$ .................................... C07D 487/22
[52] U.S. Cl. ................................................. 540/145
[58] Field of Search .................................... 540/145

[56] References Cited

U.S. PATENT DOCUMENTS

| | | | |
|---|---|---|---|
| 3,517,026 | 6/1970 | Yalman | 540/145 |
| 3,579,535 | 5/1971 | Yalman | 540/145 |
| 4,892,941 | 1/1992 | Dolphin et al. | 540/145 |
| 4,900,871 | 2/1990 | Ellis, Jr. et al. | 568/399 |
| 4,970,348 | 11/1990 | Ellis, Jr. et al. | 568/399 |
| 5,120,882 | 6/1992 | Ellis, Jr. et al. | 568/910 |

OTHER PUBLICATIONS

Ellis and Lyons, "Halogen Substituent Effects on the Catalytic Activity of Iron Porphyrin Complexes for the Selective Air-Oxidation of Alkanes in the Liquid Phase", *Cat. Lett.*, 3, 389, 1989.

Lyons and Ellis, "Selective Low Temperature Hydroxylation of Isobutane by Molecular Oxygen Catalyzed by an Iron Perhaloporphyrin Complex", *Cat. Lett.*, 8, 45, 1991.

Badger, Jones and Laslett, Porphyrins VII. The Synthesis of Porphyrins by the Rothemund Reaction, *Aust. J. Chem.*, 17, 1028, 1964.

Lindsey and Wagner, Investigation of the Synthesis of Ortho-Substituted Tetraphenylporphyrins, *J. Org. Chem.*, 54, 828, 1989.

Adler, Longo, Kampos and Kim, On the Preparation of Metalloporphyrins, *J. Inorg. Nucl. Chem.*, 32, 2443, 1970.

Traylor and Tsuchiya, Perhalogenated Tetraphenylhemins: Stable Catalysts of High Turnover Catalytic Hydroxylations, *Inorg. Chem.*, 26, 1338, 1987.

Tsuchiya and Seno, Novel Synthetic Method of Phenol from Benzene Catalysed by Perfluorinated Hemin, *Chem. Lett.*, 263, 1989.

Kuroda, Murase, Suzuki and Ogoshi, A New Route for Meso-Substituted Porphyrin, *Tet. Lett.*, 30, 2411, 1989.

Triebs and Jacob, Benzoylierungen in der Pyrrol-Reihe, II, *Liebigs Ann. Chem.*, 733, 27, 1970 (with English abstract).

Allen, Kwong-Chip, Lin, Nguyen and Tidwell, Formation and Reactivity of 1-pyrrolyl-2,2,2-trifluoroethyl Cations, *Canad. J. Chem.*, 68, 1709, 1990.

J. Chem. Soc. Perkin Trans. I (C,B); No. 4; (1974); pp. 531–534.

*Primary Examiner*—Marianne M. Cintins
*Assistant Examiner*—Michael B. Hydorn
*Attorney, Agent, or Firm*—Q. Todd Dickinson

[57] ABSTRACT

The hydroxyl group in a pyrrolic compound having in the 2-position thereof a group having the formula R(OH)CH—R is hydrocarbyl or substituted hydrocarbyl, is replaced by a group, for example a p-nitrobenzoate group, having better leaving properties than those of hydroxyl for a subsequent self-condensation and cyclization of the pyrrolic compound to form a meso-hydrocarbyl or meso-substituted hydrocarbyl porphyrin.

6 Claims, No Drawings

SYNTHETIC ROUTE TO MESO-TETRA HYDROCARBYL OR SUBSTITUTED HYDROCARBYL PORPHYRINS AND DERIVATIVES

The Government of the United States of America has rights in this invention pursuant to Cooperative Agreement No. DE-FC21-90MC26029 awarded by the U.S. Department of Energy.

This invention provides a new and improved method for the preparation of meso-hydrocarbyl or substituted halohydrocarbyl porphyrins, their β-substituted derivatives and metal complexes.

BACKGROUND OF THE INVENTION

Electron deficient metalloporphyrins (metal complexes of $3: R=C_6F_5, X, Y=F, Cl$ or $Br$)

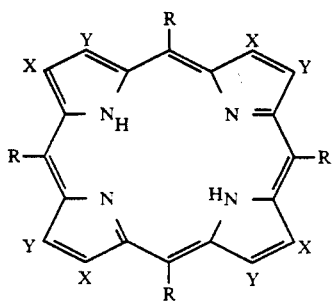

have been shown to be efficient catalysts for the oxidation of hydrocarbons with air in the liquid phase (Ellis and Lyons, Cat. Lett., 3, 389 1989; Lyons and Ellis, Cat. Lett. 8, 45 1991; U.S. Pat. Nos. 4,900,871; 4,970,348). Porphyrins 3 have been prepared by the condensation of unsubstituted pyrrole (1:X,Y=H)

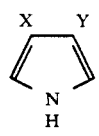

with the appropriate benzaldehyde (2: e.g. $R=C_6F_5$)

to give the meso-tetraphenylporphyrin (3:e.g. $R=C_6F_5, X, Y=H$; Badger, Jones and Laslett, *Aust. J. Chem.*, 17, 1028, 1964; Lindsey and Wagner, *J. Org. Chem.* 54, 828, 1989) followed by metal insertion [Adler, Longo, Kampos and Kim; *J. Inorg. Nucl. Chem.* 32 2443 (1970)] and β-halogenation (U.S. Pat. Nos. 4,892,941; 4,970,348; U.S. patent application Ser. No. 07/568116; Traylor and Tsuchiya, *Inorg. Chem.*, 26, 1338, 1987; Tsuchiya and Seno, *Chem. Lett.*, 263 (1989)). Porphyrins of the type 3 where R=alkyl or phenyl (X,Y=H) have also been prepared by self-condensation of 2-(1-hydroxyalkyl)pyrroles 4 ($R=CH_3$, $C_6$, $H_5$ etc.)

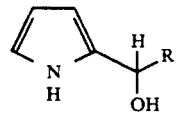

in acid medium (Kuroda, Murase, Suzuki and Ogoshi, *Tet. Lett.* 30, 2411 1989).

Acid catalyzed condensation of pyrrole 1 (X, Y=H) and perfluoroalkyl aldehyde 2 ($R=C_nF_{2n+1}$) produce meso-tetra(perfluoroalkyl)porphyrins 3 ($R=C_nF_{2n+1}; X,Y=H$) in very low yield (U.S. Pat. Nos. 4,970,348; 5,120,882). The self condensation of 2-(2-hydroxy-1,1,1-trifluoroethyl)pyrrole according to the method reported above by Kuroda et al or under the usual acid catalysis systems do not produce the corresponding porphyrin 3 ($R=CF_3$; X,Y=H). The failure of 4 where R is perfluoroalkyl to produce the porphyrin 3 can be attributed to its inability to generate the corresponding carbocation intermediate 5 by the elimination of the hydroxyl group.

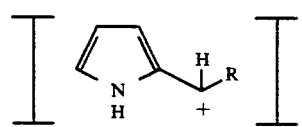

DESCRIPTION OF THE INVENTION

This invention provides a method for the conversion of pyrroles of the type 4 (R=hydrocarbyl or substituted hydrocarbyl such as halohydrocarbyl or halocarbyl, for example $C_nF_{2n+1}$), to the corresponding porphyrin 3 (R=hydrocarbyl or substituted hydrocarbyl such as halohydrocarbyl or halocarbyl, for example $C^mF_{2n+1}$; X,Y=H) by the prior activation of the hydroxyl group. This is effected by its conversion to a better leaving group L in 6

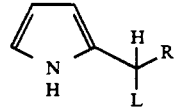

followed by self-condensation/cyclization. The activated leaving group L is in general a reactive ester such as benzoate, p-nitrobenzoate, p-toluenesulfonate (tosylate), p-bromobenzenesulfonate (brosylate), p-nitrobenzenesulfonate (nosylate), methanesulfonate (mesylate) and trifluoromethanesulfonate (triflate). By varying the L group, it is possible to vary the stability/reactivity of the precursor pyrrole 6 and hence the yield of the porphyrin 3. Pyrroles of the type 4 required for this synthesis are conveniently prepared by the acylation of pyrrole with the appropriate perfluoroalkylcarboxylic anhydride [Triebs and Jacob; *Liebigs Ann. Chem.*, 733 27 (1970); Allen, Kwong-Chip, Lin, Nguyen and Tidwell; *Canad. J. Chem.* 68 1709 (1990)] and the subsequent reduction to the alcohol [Allen, Kwong-Chip, Lin, Nguyen and Tidwell; *Canad. J. Chem.*, 68 1709 (1990)].

The method of the invention starts with a pyrrolic compound (4) which has, as shown in 4, an R(OH)-CH—group in the 2-position of the pyrrolic compound, where R is hydrocarbyl or substituted hydrocarbyl. In the method of the invention, the OH group of such compound is replaced by a group having better leaving properties than those of hydroxyl for subsequent self-condensation and cyclization of the pyrrolic compound to form a meso-hydrocarbyl, meso-halohydrocarbyl or meso-halocarbyl porphyrin. The invention is particularly useful in connection with the halocarbyl compounds, in which, unlike the hydrocarbyl compounds, OH is not a satisfactory leaving group. Examples of halocarbyl groups are perhaloalkyl groups such as perfluoromethyl, perfluoroethyl and the like, and haloaryl groups such as perfluorophenyl and the like. Examples of hydrocarbyl groups are aryl groups such as phenyl, substituted phenyl and the like, and alkyl or cycloalkyl groups such as methyl, ethyl, cyclohexyl and the like.

The pyrrolic compound 4 may be obtained for example by conversion of a pyrrole to an acetylpyrrole, and conversion of the latter to a hydroxyethylpyrrole, compound 4, as described in the examples below.

In the method of the invention, the pyrrolic compound starting material has the formula:

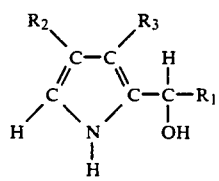

where $R_2$ and $R_3$ are, independently, hydrogen or an electron-withdrawing group, and $R_1$ is hydrocarbyl or substituted hydrocarbyl. The hydroxyl group of such pyrrolic compound is converted to a leaving group having better leaving properties than those of hydroxyl, thereby to produce a pyrrolic compound containing said leaving group. The leaving group is then removed and the pyrrolic compound cyclized to produce a meso-hydrocarbyl or substituted hydrocarbyl porphyrin. A better leaving group than hydroxyl refers to a group which, at least in the case where $R_4$ in the above formula is trifluoromethyl, has better leaving properties than those of hydroxyl.

In one embodiment of the invention, the leaving group is an organic ester group. In one embodiment, whether or not the leaving group is an organic ester group, the electron-deficient R group is selected from the group consisting of halogen, halohydrocarbyl, halocarbyl, nitro or cyano.

The porphyrins 3 (X, Y=F,Cl,Br) are obtained from the initially prepared β-unsubstituted porphyrins 3 (X,Y=H) by metallation followed by halogenation according to prior art cited above.

The meso-hydrocarbyl or substituted hydrocarbyl porphyrins produced by the method of the invention may be converted to β-substituted derivations and metal complexes thereof by known methods.

The following examples illustrate the invention.

The examples concern the synthesis of meso-tetra(trifluoromethyl)porphyrin 3 (R=CF$_3$; X,Y=H) using the activated pyrrole 6 (L=—OC$_6$H$_4$4—NO$_2$).

EXAMPLE 1

The starting material for the method of the invention was prepared as follows.

Pyrrole 7
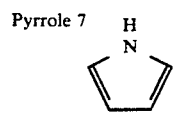

was reacted (over a 4h period), with an equimolar quantity of trifluoroacetic anhydride in benzene under an inert atmosphere at 2°-3° C. The reaction mixture was diluted with water, the organic phase washed with aqueous sodium bicarbonate and water and the trifluoroacetylpyrrole 8

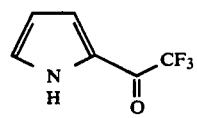

isolated in over 75% yield by evaporation of the solvent; m.pt 45°–46° C.; mass spectrum: m/z=163 (M+).

Trifluoroacetylpyrrole 8 in methanol was reacted with solid sodium borohydride (in portions) at 0°-5° C. The reaction mixture was treated with saturated solution of sodium bicarbonate and the hydroxyethylpyrrole 9 was extracted into ether. The ether solution was washed with aqueous sodium bicarbonate, water, dried and the product isolated in over 90% yield by evaporation of the solvent; mass spectrum: m/z=165 (M+)

EXAMPLE 2

The p-nitrobenzoate 10

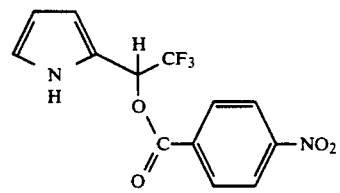

was prepared by the reaction of the pyrrole 9

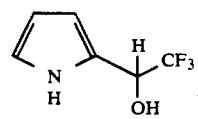

(5 mmol in anhydrous ether below 10°) with a solution of p-nitrobenzoyl chloride (5 mmol) in ether in the presence of triethylamine. The product 10 was too reactive/unstable to be isolated and characterized but a gas chromatograph mass spectrum (GCMS) of the reaction mixture indicated the formation of 10; m/z=313 (M+-1), 145(carbocation 5; R—CF$_3$). The reaction mixture was treated directly with acid to effect the tetramerization and cyclization via two methods as described below.

EXAMPLE 3

The ether solution of 10 prepared above (ca.50 mL), was diluted with propanoic acid (total volume 500 mL), treated with zinc acetate (300 mg) and heated at reflux for 3 h. The reaction mixture was diluted with chloroform and the acid was extracted out with water and aqueous sodium bicarbonate. The crude product was purified by chromatography on alumina to give meso-tetra(trifluoromethyl)porphinato zinc 11

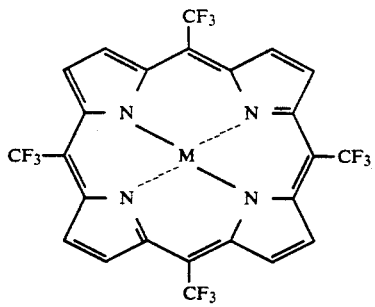

(mass spectrum: m/z=644 M+; absorption spectrum: 398-Soret, 530, 588 nm) and the non-metallated porphyrin 12 in up to 2% overall yield.

EXAMPLE 4

The ether solution of 10 as prepared above (ca. 50 mL) was diluted with chloroform (total volume 500 mL), degassed, treated with 660μL of boron trifluoride etherate (2.5M) and heated at reflux for 2 h. The product, meso-tetra(trifluoromethyl)porphyrin 12 was isolated following oxidation of the reaction mixture and chromatography (alumina) in up to 2% yield; mass spectrum: m/z=582 (M+); absorption spectrum: 404.Soret, 508, 544, 592, 648 nm.

The invention claimed is:

1. Method for the synthesis of a porphyrin which comprises:
   (a) converting the hydroxyl group of a compound having the formula:

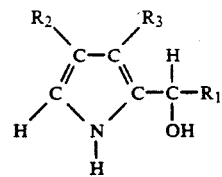

where $R_2$ and $R_3$ are, independently, hydrogen or an electron-deficient group, and $R_1$ is hydrocarbyl or substituted hydrocarbyl; to a leaving group having better leaving properties than those of hydroxyl, thereby to produce a pyrrolic compound containing said leaving group, and
   (b) removing said leaving group and cyclizing said pyrrolic compound to produce a porphyrin.

2. Method according to claim 1 wherein said leaving group is an organic ester group.

3. Method according to claim 1 wherein said electron-deficient group is selected from the group consisting of halogen, halohydrocarbyl, nitro and cyano.

4. Method according to claim 1 wherein $R_1$ haloalkyl.

5. Method according to claim 1 wherein said leaving group is a carboxylate or sulfonate ester.

6. Method according to claim 1 wherein, $R_2$ and $R_3$ are hydrogen, $R_1$ is trifluoromethyl and said leaving group is p-nitrobenzoate.

* * * * *